US00PP35356P2

(12) United States Plant Patent
Snijder

(10) Patent No.: US PP35,356 P2
(45) Date of Patent: Aug. 29, 2023

(54) ***VERBENA* PLANT NAMED 'VEAZ0065'**

(50) Latin Name: *Verbena hybrida*
Varietal Denomination: VEAZ0065

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/468,816

(22) Filed: Sep. 8, 2021

(30) Foreign Application Priority Data

Jun. 15, 2021 (QZ) ..... 2021/1601

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 5/02
See application file for complete search history.

(56) References Cited

PUBLICATIONS https://online.plantvarieties.eu/publicSearch?denomination=VEAZ0065; Nov. 3, 2021; 3 pages.*

* cited by examiner

*Primary Examiner* — Kent L Bell
(74) *Attorney, Agent, or Firm* — Dale Skalla

(57) ABSTRACT

A new *Verbena* plant named 'VEAZ0065' particularly distinguished by medium sized inflorescences, light-green flowers, and a semi-trailing plant habit.

1 Drawing Sheet

Latin name of the genus and species of the plant claimed: *Verbena hybrida.*

Varietal denomination: 'VEAZ0065'.

BACKGROUND OF THE NEW PLANT

The present invention comprises a new *Verbena*, botanically known as *Verbena hybrida*, and hereinafter referred to by the variety name 'VEAZ0065'.

'VEAZ0065' is a product of a planned breeding program. The new cultivar has medium sized inflorescences, light-green flowers, and a semi-trailing plant habit.

'VEAZ0065' originated from a self-pollination made in September 2015 in the greenhouse in Enkhuizen, The Netherlands.

The parent was an unpatented proprietary plant designated 'T0717-4V', having smaller flowers.

The resulting seed was sown in February 2016 in a greenhouse in Enkhuizen, The Netherlands, and 'VEAZ0065' was selected as one flowering plant within the progeny of the stated cross in May 2016.

The first act of asexual reproduction of 'VEAZ0065' was accomplished when vegetative cuttings were propagated from the initial selection in June 2016 in a greenhouse in Enkhuizen, The Netherlands.

BRIEF SUMMARY OF INVENTION

Horticultural examination of plants grown from cuttings of the plant initiated in the fall of 2016, and continuing thereafter, has demonstrated that the combination of characteristics as herein disclosed for 'VEAZ0065' are firmly fixed and are retained through successive generations of asexual reproduction.

'VEAZ0065' has not been observed under all possible environmental conditions. The phenotype may vary significantly with variations in environment such as temperature, light intensity, and day length.

A Plant Breeder's Right for this cultivar was applied for in the European Union by the Assignee, Syngenta Crop Protection, AG, on Jun. 15, 2021, No. 2021/1601. The first offer for sale occurred Jan. 19, 2021 by Syngenta Crop Protection, AG who obtained 'VEAZ0065' and all information thereto directly from the inventor, Ronald Snijder. This sale falls within the exception allowed under 35 U.S.C. 102 (b)(1).

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0065' with colors being as true as possible with an illustration of this type.

Figure 1:
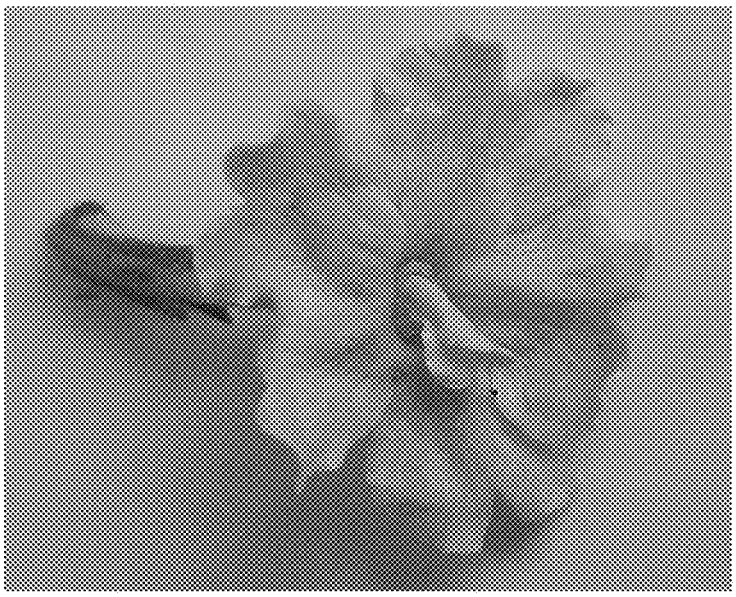
Figure 2:
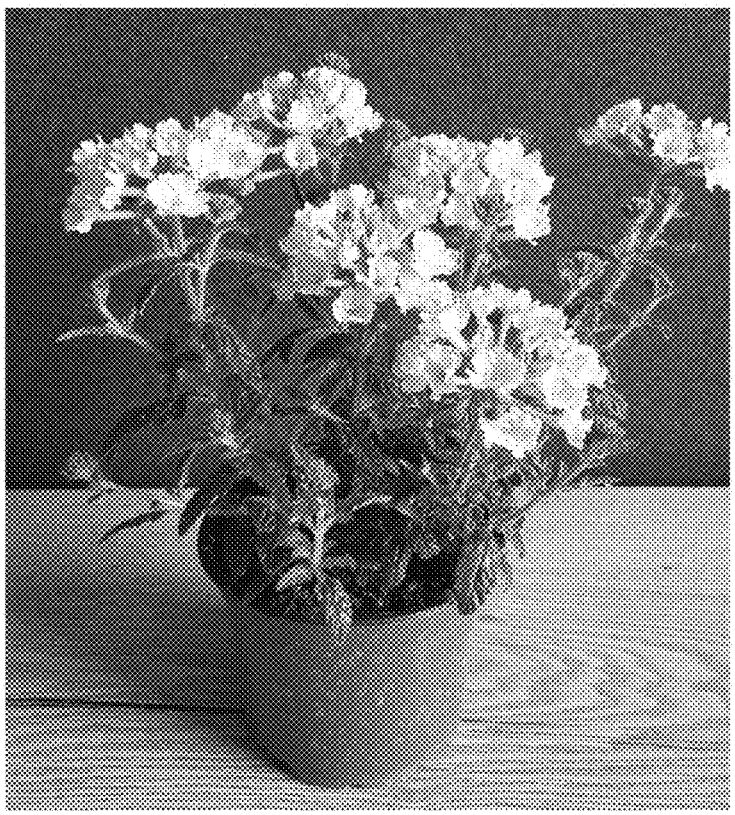

The photographic drawing in FIG. 1 shows a close view of an inflorescence of the new plant, and in FIG. 2 a whole flowering plant.

The aforementioned photographs were taken in late May 2018 in Andijk, The Netherlands. The plants were about 10 weeks old and were grown in 11 cm pots.

DETAILED BOTANICAL DESCRIPTION

Colour references are made to The Royal Horticultural Society (RHS) Colour Chart 2001.

TABLE 1

DIFFERENCES BETWEEN THE NEW VARIETY 'VEAZ0065' AND A MOST SIMILAR VARIETY

| | 'VEAZ0065' | 'VEAZ0013' (U.S. Plant Pat. No. 24,386) |
|---|---|---|
| Plant habit: | Semi-trailing | Upright |
| Color upper side petal: | Between RHS 145C and RHS 145D | Between RHS 150C and RHS 150D |

Plant:

*Form, growth and habit.*—Herbaceous, initially upright, then outwardly spreading; vigorous and free branching.

*Plant height.*—12 cm.

*Plant height (inflorescence included).*—17 cm.

*Plant width.*—22 cm.

Roots:

*Number of days to initiate and produce roots.*—11-14 days at about 22 degrees C.

*Type.*—Fine, fibrous, free branching.

*Color.*—N155B but whiter.

Foliage:

*Arrangement.*—Opposite, simple.

*Immature, leaf color, upper surface.*—RHS 143B.

*Immature, leaf color, lower surface.*—RHS 141C.

*Mature, leaf color, upper surface.*—RHS 137A.

*Mature, leaf color, lower surface.*—RHS 138A.

*Length.*—3-4 cm.

*Width.*—1-1.5 cm.

*Shape.*—Lanceolate.

*Base shape.*—Decurrent.

*Apex shape.*—Acute.

*Margin.*—Dentate.

*Texture, upper surface.*—Hirsute.

*Texture, lower surface.*—Hirsute.

*Color of veins, upper surface.*—RHS 137A.

*Color of veins, lower surface.*—RHS 138A.

*Pattern of veining.*—Pinnate.

*Petiole color.*—RHS 137A.

*Petiole length.*—0-0.1 cm.

*Petiole width.*—0-0.3 cm.

*Texture.*—Hirsute.

Stem:

*Branching characteristics.*—Makes branches on every node.

*Quantity of main branches per plant.*—6-12.

*Color of stem.*—RHS 143C.

*Stem length.*—10-13 cm.

*Stem width.*—About 0.3 cm.

*Length of internodes.*—1-3 cm.

*Texture.*—Hirsute.

*Color of peduncle.*—RHS 143C.

*Length of peduncle.*—4-5 cm.

*Peduncle diameter.*—0.2 cm.

*Texture.*—Canescent.

Inflorescence:

*Type.*—Umbel-like, but actually a spike, umbrella-shaped, large.

*Blooming habit.*—Flowers continuously through the summer months.

*Lastingness of individual blooms on the plant.*—About 7 days in the greenhouse.

*Fragrance.*—None.

*Number of inflorescences per plant.*—20-30 at various stages.

*Horizontal diameter of inflorescence.*—About 5 cm.

*Depth of inflorescence.*—4.5 cm.

*Number of florets per inflorescence (including any buds at the time).*—25-30.

Bud (just when opening/showing color):

*Color.*—RHS 145B.

*Length.*—1 cm.

*Width.*—0.4 cm.

*Shape.*—Tubular with a bulbous end.

Floret:

*Form.*—Sessile; salver-shape, composed of 5 partly fused petals with a base of a narrow tube.

*Immature color, upper surface.*—RHS 145C, bit darker, RHS 145B, at the apex.

*Immature color, lower surface.*—RHS 145C.

*Mature color, upper surface.*—RHS 145C slightly fading to RHS 145D by age.

*Mature color, lower surface.*—RHS 145D.

*Floret diameter.*—1.5 cm.

*Floret length (depth).*—2.5 cm.

*Number of petals.*—Gamopetalous, 5 lobed; some florets with a petaloid.

*Petal length.*—0.7-0.8 cm.

*Petal width.*—0.7 cm.

*Shape.*—Obcordate.

*Apex shape.*—Emarginate.

*Margin.*—Entire.

*Petal texture, upper surface.*—Smooth.

*Petal texture, lower surface.*—Papillose.

*Corolla tube length.*—1.7-1.9 cm.

*Corolla tube width.*—0.2 cm.

*Corolla tube color inside.*—RHS 145D.

*Tube color outside.*—RHS 145D.

*Corolla texture, inside.*—Papillose.

*Corolla texture, outside.*—Glabrous.

*Throat hair color.*—RHS 155A.

Calyx:

*Type.*—Five sepals whose margins are fused to each other along their length, with a transparent membrane of less than 0.1 cm in width and with one smaller sepal attached to the base of the calyx.

*Color of sepals.*—RHS 138B, striped RHS 138A.

*Length of sepals.*—1-1.2 cm.

*Width of sepals.*—0.25 cm.

*Sepal shape.*—Linear, but fused.

*Apex shape.*—Acute.

*Margins.*—Entire.

*Texture.*—Densely covered with short hair.

Reproductive organs:

*Gynoecium.*—

*Pistil.*—1.

*Pistil length.*—1.3 cm.

*Style color.*—RHS N157A.

*Style length.*—1.5 cm.

*Stigma color.*—RHS 144A.

*Ovary color.*—RHS 144B.

*Ovary length.*—0.22 cm.

*Ovary width.*—0.1 cm.

*Androecium.*—

*Stamens*.—Anthers and filaments fused to upper half of corolla tube; four anthers with two pollen sacs per anther.

*Color of filaments*.—RHS 154D.

*Filament length*.—0.25 cm.

*Anther color*.—RHS 153D.

*Anther length*.—0.15 cm.

*Pollen amount*.—Abundant.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0065' substantially as illustrated and described herein.

* * * * *